United States Patent [19]

Kubota et al.

[11] 4,405,736

[45] Sep. 20, 1983

[54] 2,2,6,6-TETRAMETHYL-4-PIPERIDYL SPIRO ALIPHATIC ETHERS AND STABILIZERS FOR SYNTHETIC POLYMERS

[75] Inventors: Naohiro Kubota, Ageo; Toshihiro Shibata, Omiya; Kazuo Sugibuchi, Tokyo; Yutaka Nakahara, Iwatsuki, all of Japan

[73] Assignee: Adeka Argus Chemical Co., Ltd., Urawa, Japan

[21] Appl. No.: 271,888

[22] Filed: Jun. 9, 1981

[30] Foreign Application Priority Data

Jun. 23, 1980 [JP] Japan ................................. 55-84714

[51] Int. Cl.$^3$ .................... C07D 491/113; C08K 5/34; C08K 5/35
[52] U.S. Cl. ..................................... 524/102; 546/13; 546/19; 546/14; 524/103
[58] Field of Search .................. 524/102, 103; 546/19, 546/13, 14

[56] References Cited

U.S. PATENT DOCUMENTS 4,237,294  12/1980  Soma et al. ........................... 546/19

*Primary Examiner*—Robert T. Bond

[57] ABSTRACT

2,2,6,6-Tetramethyl-4-piperidyl spiro aliphatic ethers are provided, useful as stabilizers for organic polymeric materials.

44 Claims, No Drawings

2,2,6,6-TETRAMETHYL-4-PIPERIDYL SPIRO ALIPHATIC ETHERS AND STABILIZERS FOR SYNTHETIC POLYMERS

Minagawa, Kubota and Shibata, U.S. Pat. No. 4,128,608, patented Dec. 5, 1978, provide 2,2,6,6-tetramethyl-4-piperidyl spiro aliphatic ethers useful as stabilizers for organic polymeric materials, and having the general formula:

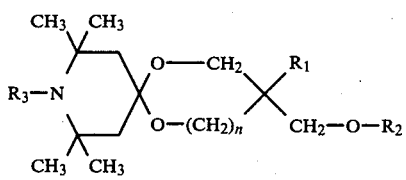

wherein:

$R_1$ is selected from the group consisting of hydrogen; lower alkyl and lower hydroxyalkyl having one or two carbon atoms;

$R_2$ is

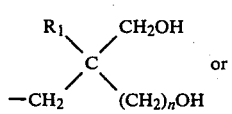 or

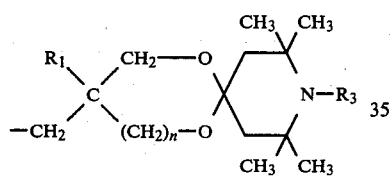

$R_3$ is selected from the group consisting of hydrogen and O; and n is 0 to 1.

Minagawa, Kubota and Shibata, U.S. Pat. No. 4,173,599, patented Nov. 6, 1979, provide 2,2,6,6-tetraalkyl-4-piperidyl ketones and ketals useful as stabilizers for organic polymeric materials, and having the general formula:

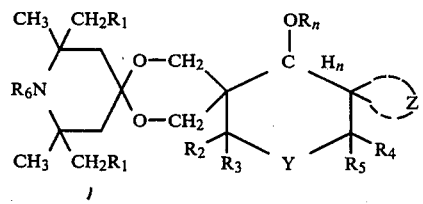

wherein:

n are each 0 or 1 and are each the same;

R is selected from the group consisting of hydrogen; alkyl having from one to about eighteen carbon atoms, and acyl

R′ being alkyl having from one to about eighteen carbon atoms;

$R_1$, $R_2$, $R_3$, $R_4$ and $R_5$ are selected from the group consisting of hydrogen and alkyl having from one to about eighteen carbon atoms;

$R_6$ is selected from the group consisting of hydrogen and O;

Y is selected from the group consisting of a carbon-to-carbon bond—, oxy—O—; alkylene having from one to about three carbon atoms, and alkyl-substituted alkylene, the alkylene having from one to about three carbon atoms, the alkyl having from one to about six carbon atoms; and Z is selected from the group consisting of:

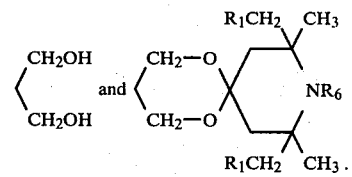

In accordance with the instant invention, 2,2,6,6-tetramethyl-4-piperidyl spiro aliphatic ethers are provided, useful as stabilizers for organic polymeric material, and having the general formula:

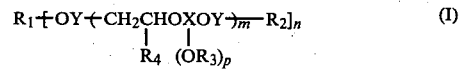

wherein:

Y is

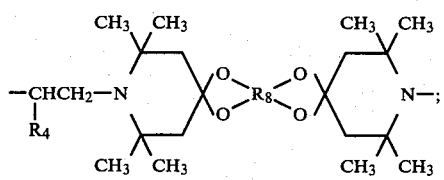

X is selected from the group consisting of alkylene having from one to about eighteen carbon atoms; cycloalkylene having from three to about eight carbon atoms; arylene having from about six to about eighteen carbon atoms; polyacyl

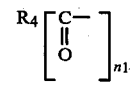

wherein $n_1$ is a number from 2 to 4; polycarbamoyl

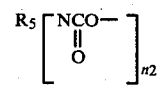

wherein $n_2$ is a number from 2 to 4;

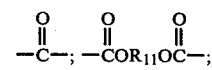

and di- and trivalent oxyacid groups;

$R_1$ is selected from the group consisting of hydrogen,

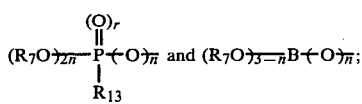

$R_2$ is selected from the group consisting of hydrogen and

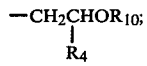

$R_3$ is selected from the group consisting of alkyl having from one to about eighteen carbon atoms; cycloalkyl having from three to about eight carbon atoms; aryl having from about six to about eighteen carbon atoms; and —X—O—$R_1$;

$R_4$ is selected from the group consisting of hydrogen; aliphatic having from one to about eighteen carbon atoms; cycloaliphatic having from three to about eight carbon atoms; heterocyclic having from six to about eighteen carbon atoms; and aromatic having from six to about eighteen carbon atoms;

$R_5$ is selected from the group consisting of aliphatic having from one to about eighteen carbon atoms; cycloaliphatic having from three to about eight carbon atoms; heterocyclic having from six to about eighteen carbon atoms; and aromatic having from six to about eighteen carbon atoms;

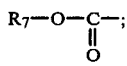

and monovalent oxyacid groups;

$R_7$ is selected from the group consisting of the residues of monohydric alcohols having from one to about eighteen carbon atoms and phenols having from six to about fifty carbon atoms;

$R_6$ is selected from the group consisting of

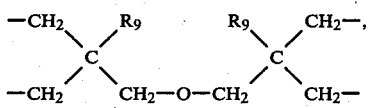

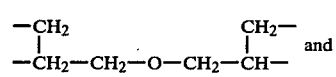

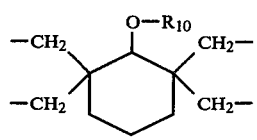

$R_9$ is selected from the group consisting of aliphatic $R_5$ and cycloaliphatic $R_5$; and —CH$_2$O$R_{10}$;

$R_{10}$ is selected from the group consisting of hydrogen,

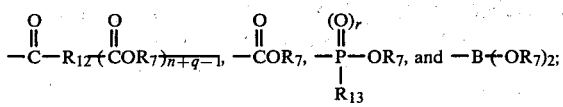

$R_{11}$ is selected from the group consisting of alkylene and oxyalkylene having from two to about ten carbon atoms and from zero to about five oxyether groups; cycloalkylene having from three to about eight carbon atoms; and arylene having from six to about fifty carbon atoms; and isocyanurate;

$R_{12}$ is the residue of mono-, di, tri- or tetracarboxylic acid;

$R_{13}$ is selected from the group consisting of hydrogen, $R_5$, and —O—$R_5$;

m is a number from zero to 10;
n is a number from zero to 4;
p is zero or 1;
q is a number from zero to 3; and
r is zero or 1.

In formula (I), exemplary $R_3$, $R_4$, $R_5$, $R_9$ and $R_{13}$ alkyl include methyl, ethyl, propyl, butyl, octyl, 2-ethylhexyl, isooctyl, decyl, dodecyl, tetradecyl, octadecyl; exemplary $R_3$, $R_4$, $R_5$, $R_9$ and $R_{13}$ cycloalkyl include cyclobutyl, cyclopropyl, cyclopentyl, cyclohexyl, cycloheptyl and cyclooctyl; exemplary $R_3$, $R_4$, $R_5$, $R_9$ and $R_{13}$ aryl include benzyl, phenylethyl, phenyl, toluyl, xylyl, butylphenyl and nonylphenyl.

Exemplary $R_7$ are the residues of monohydric alcohols such as methanol, ethanol, isopropanol, butanol, pentanol, cyclohexanol, octanol, 2-ethylhexanol, isooctanol, nonanol, decanol, isodecanol, lauryl alcohol, tridecanol, myristyl alcohol, palmityl alcohol, steryl alcohol, mono-, di-, and triethylene glycol monoether, benzyl alcohol and phenyl ethanol; and the residue of monohydric phenols such as phenol, cresol, 4-t-butylphenol, octylphenol, nonylphenol, chlorphenol, 2,6-dimethylphenol, 2-cyclohexylphenol, 2,4-di-t-butylphenol, 2-t-butyl-4-methylphenol and dinonylphenol.

Exemplary $R_{11}$ alkylene are the residues of polyhydric alcohols such as ethylene glycol, diethylene glycol, triethylene glycol, 1,2-propanediol, 1,3-propanediol, 1,2-butanediol, 1,3-butanediol, 1,4-butanediol, neopentyl glycol, thiodiethylene glycol, 1,6-hexanediol, 1,10-decanediol, 1,4-cyclohexanediol, 1,4-cyclohexanedimethanol, 1,4-phenyldimethanol, hydrogenated Bisphenol-A, glycerol, trimethylolmethane, trimethylolethane, and tris (2-hydroxyethyl) isocyanurate; exemplary arylene are derived from polyhydric phenols such as hydroquinone, 4,4'-isopropylidene diphenol (Bisphenol A), 4,4'-cyclohexylidenediphenol, 4,4'-methylenebisphenol, 4,4'-sulfobisphenol, 2,5-di-t-butylhydroquinone, 2,3,6-trimethyl hydroquinone, 2-methylresorcinol, 2,2'-methylene bis(4-methyl-6-t-butylphenol), 2,2'-methylene bis(4-ethyl-6-t-butylphenol), 2,2'-methylene bis[4-methyl-6-(α-methylcyclohexyl)phenol], 2,2'-n-butylidenebis(4,6-di-methylphenol), bis-1,1-(2'-hydroxy-3',5'-di-methylphenyl)-3,5,5-trimethylhexane, 2,2'-cyclohexylidene-bis-(4-ethyl-6-t-butylphenol), 2,2'-isopropyl-benzylidene-bis-(4-ethyl-6-t-butylphenol), 2,2'-thiobis-(4-t-butyl-6-methylphenol), 2,2'-thiobis-(4-methyl-6-t-butylphenol), 2,2'-thiobis (4,6-di-t-butylphenol), 4,4'-methylene-bis-(2-methyl-6-t-butylphenol), 4,4'-isopropylidene-bis-(2-phenylethylphenol), 4,4'-n-butylidene-bis-(3-methyl-6-t-butylphenol), 4,4'-cyclohexylidene-bis-(2-t-butylphenol), 4,4'-cyclohexylidene-bis-(2-t-butylphenol), 4,4'-cyclohexylidene-bis-(2-cyclohexylphenol), 4,4'-benzylidene-bis-(2-t-butyl-5-methylphenol), 4,4'-oxobis-(3-methyl-6-isopropylphenol), 4,4'-thiobis-(2-methyl-6-t-butylphenol), 4,4'-thiobis-(3-methyl-6-t-butylphenol), 4,4'-sulfobis-(3-methyl-6-t-butylphenol), bis-(2-methyl-4-hydroxy-5-t-butylbenzyl)-sulfide, 1,1,3-tris-(2'-methyl-4'-hydroxy-5'-t-butylphenyl)butane, 2,2'-bis(3'-t-butyl-4'-hydroxyphenyl)-4-(3'',5''-di-t-butyl-4'''-hydroxyphenyl)butane and 2,2'-bis-(2'-methyl-5'-t-butyl-4'-hydroxyphenyl)-4-(3'',5''-di-t-butyl-4'-hydroxyphenyl) butane.

Exemplary $R_{12}$ are the residues of mono-, di-, tri-, and tetracarboxylic acids such as formic acid, acetic acid, propionic acid, butyric acid, pivalic acid, 2-ethylhexanoic acid, lauric acid, palmitic acid, stearic acid, acrylic acid, crotonic acid, oleic acid, acetoacetic acid, levulinic acid, pyruvic acid, ketostearic acid, aminoacetic acid, dodecyl mercaptopropionic acid, 3,5-di-t-butyl-4-hydroxyphenyl-propionic acid; benzoic acid, toluic acid, 4-t-butylbenzoic acid, 3,5-di-t-butyl-4-hydroxybenzoic acid, nicotinic acid, isonicotinic acid, 2,2,6,6-tetramethyl-piperidine-4-carboxylic acid, 3,8,8,10,10-pentamethyl-9-aza-1,5-dioxaspiro[5,5]undecane-3-carboxylic acid, oxalic acid, malonic acid, succinic acid, glutaric acid, adipic acid, sebacic acid, dodecane dicarboxylic acid, eicosane dicarboxylic acid, tartaric acid, maleic acid, phthalic acid, isophthalic acid, terephthalic acid, iminodiacetic acid, thiodipropionic acid, diglycolic acid, tetrahydrophthalic acid, endomethylenetetrahydrophthalic acid, thiophenedicarboxylic acid, furanedicarboxylic acid, dicarboxyethyl piperidine, citric acid, tricarballylic acid, butanetricarboxylic acid, butenetricarboxylic acid, trimellitic acid, ethylenetetracarboxylic acid, ethanetetracarboxylic acid, 1,2,2,3-propanetetracarboxylic acid and 1,1,2,3-propanetetracarboxylic acid.

Exemplary X alkylene are methylene, ethylene, propylene, butylene, hexamethylene and cyclohexylene; arylene are phenylene, and biphenylene; polyacyl are the polyacyl groups derived from di- or polycarboxylic acid such as oxalic acid, malonic acid, succinic acid, glutaric acid, adipic acid, sebacic acid, dodecanedicarboxylic acid, eicosanedicarboxylic acid, tartaric acid, maleic acid, phthalic acid, isophthalic acid, terephthalic acid, iminodiacetic acid, thiodipropionic acid, diglycolic acid, tetrahydrophthalic acid, endomethylene tetrahydrophthalic acid, thiophene dicarboxylic acid, furane dicarboxylic acid, dicarboxyethylpiperidine, citric acid, tricarballylic acid, butanetricarboxylic acid, butenetricarboxylic acid, trimellitic acid, ethylene tetracarboxylic acid, ethane tetracarboxylic acid, 1,2,2,3-propane-tetracarboxylic acid and 1,1,2,3-propane-tetracarboxylic acid.

Exemplary X polycarbamoyl are the carbamoyl groups derived from diisocyanates such as hexamethylenediisocyanate, lysinediisocyanate, phenyldiisocyanate, toluylenediisocyanate, diphenyletherdiisocyanate, xylylenediisocyanate, 3-isocyanatomethyl-3,5,5-trimethylcyclohexylisocyanate, bis-(isocyanatomethyl)cyclohexane and 3-(2'-isocyanatocyclohexyl)-propylisocyanate.

Exemplary monovalent groups from oxyacid are the monovalent groups derived from phosphorus-containing oxyacids such as phosphorous acid, phosphoric acid, (organic) phosphonous acid, (organic) phosphonic acid, (diorganic) phosphinous acid, and (diorganic) phosphinic acid, (organic) silicic acid, boric acid, and esters thereof.

Exemplary $R_7$ are the residues of monohydric alcohols such as methanol, ethanol, isopropanol, butanol, pentanol, cyclohexanol, octanol, 2-ethylhexanol, isooctanol, nonanol, decanol, isodecanol, lauryl alcohol, tridecanol, myristyl alcohol palmityl alcohol, stearyl alcohol, mono-, di- and triethyleneglycomonoether, benzyl alcohol and phenyl ethanol; and the residues of monohydric phenols such as phenol, cresol, 4-t-butylphenol, octylphenol, nonylphenol, chlorphenol, 2,6-dimethylphenol, 2-cyclohexylphenol, 2,4-di-t-butylphenol, 2-t-butyl-4-methylphenol and dinonyl phenol.

Exemplary $R_{11}$ and X alkylene and cycloalkylene are those derived from polyhydric alcohols such as ethylene glycol, diethylene glycol, triethylene glycol, 1,2-propanediol, 1,3-propanediol, 1,2-butanediol, 1,3-butanediol, 1,4-butanediol, neopentyl glycol, thiodiethylene glycol, 1,6-hexanediol, 1,10-decanediol, 1,4-cyclohexanediol, 1,4-cyclohexanedimethanol, 1,4-phenyldimethanol, hydrogenated-Bisphenol A, glycerol, trimethylolmethane, trimethylolethane and tris-(2-hydroxyethyl)isocyanurate; exemplary $R_{11}$ arylene are those derived from polyhydric phenols such as hydroquinone, 4,4'-isopropylidenediphenol (Bisphenol A), 4,4'-cyclohexylidenediphenol, 4,4'-methylenebisphenol, 4,4'-sulfobisphenol, 2,5-di-t-butyl-hydroquinone, 2,3,6-trimethylhydroquinone, 2-methylresorcinol, 2,2'-methylenebis-(4-methyl-6-t-butylphenol), 2,2'-methylenebis-(4-ethyl-6-t-butylphenol), 2,2'-methylenebis[4-methyl-6-(α-methylcyclohexyl)phenol]], 2,2'-n-butylidenebis(4,6-di-methylphenol), bis-1,1-(2'-hydroxy-3',5'-di-methylphenyl)-3,5,5-trimethylhexane, 2,2'-cyclohexylidenebis-(4-ethyl-6-t-butylphenol), 2,2'-isopropylbenzylidenebis-(4-ethyl-6-t-butylphenol), 2,2'-thiobis-(4-t-butyl-6-methylphenol), 2,2'-thiobis-(4-methyl-6-t-butylphenol), 2,2'-thiobis-(4,6-di-t-butylphenol), 4,4'-methylene bis-(2-methyl-6-t-butylphenol), 4,4'-isopropylidenebis-2-phenylethylphenol), 4,4'-n-butylidenebis-(3-methyl-6-t-butylphenol), 4,4'-cyclohexylidenebis-(2-t-butylphenol), 4,4'-cyclohexylidenebis-(2-t-butylphenol), 4,4'-cyclohexylidenebis-(2-cyclohexylphenol), 4,4'-benzylidenebis-(2-t-butyl-5-methylphenol), 4,4'-oxobis-(3-methyl-6-isopropylphenol), 4,4'-thiobis-(2-methyl-6-t-butylphenol), 4,4'-thiobis-(3-methyl-6-t-butylphenol), 4,4'-sulfobis-(3-methyl-6-t-butylphenol), bis-(2-methyl-4-hydroxy-5-t-butylbenzyl)sulfide, 1,1,3-tris-(2'-methyl-4'-hydroxy-5'-t-butylphenyl)-butane, 2,2-bis-(3'-t-butyl-4'-hydroxyphenyl)-4-(3'',5''-di-t-butyl-4'''-hydroxyphenyl)butane and 2,2-bis-(2'-methyl-5'-t-butyl-4'-hydroxyphenyl)-4-(3'',5''-di-t-butyl-4'-hydroxyphenyl)butane.

Exemplary X polyacyl include the polyacyl groups derived from di- and higher polycarboxylic acids, such as oxalic acid, malonic acid, succinic acid, glutaric acid, adipic acid, subacic acid, dodecanedicarboxylic acid, eicosanedicarboxylic acid, tartaric acid, maleic acid, phthalic acid, isophthalic acid, terephthalic acid, iminodiacetic acid, thiodipropionic acid, diglycolic acid, tetrahydrophthalic acid, endomethylenetetrahydrophthalic acid, thiophenedicarboxylic acid, furanedicarboxylic acid, dicarboxyethylpiperidine, citric acid, tricarballylic acid, butanetricarboxylic acid, butenetricarboxylic acid, trimellitic acid, ethylenetetracarboxylic acid, ethanetetracarboxylic acid, 1,2,2,3-propanetetracarboxylic acid, and 1,1,2,3-propanetetracarboxylic acid.

Exemplary X polycarbamoyl include the polycarbamoyl groups derived from polyisocyanates such as hexamethylene diisocyanate, lysine diisocyanate, phenyl diisocyanate, toluylene diisocyanate, diphenylether diisocyanate, xylylene diisocyanate, 3-isocyanatomethyl-3,5,5-trimethylcyclohexyl isocyanate, bis-(isocyanatomethyl)cyclohexane and 3-(2'-isocyanatocyclohexyl)propylisocyanate.

Exemplary di- and trivalent oxyacid include the groups derived from phosphorous acid, phosphoric acid, (organic) phosphonous acid, (organic) phosphonic acid, boric acid, (organic) silicic acid and dimers thereof, joined by polyhydric alcohol or phenol.

Typical compounds having the formula (I) are shown below:

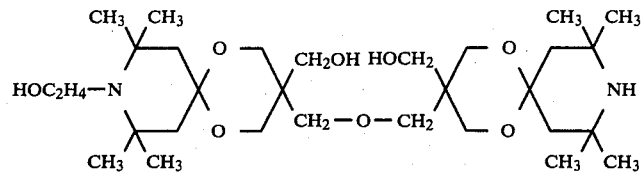

1.

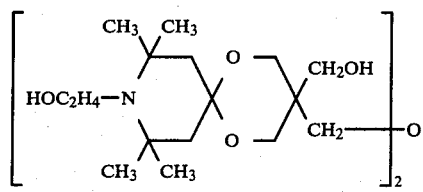

2.

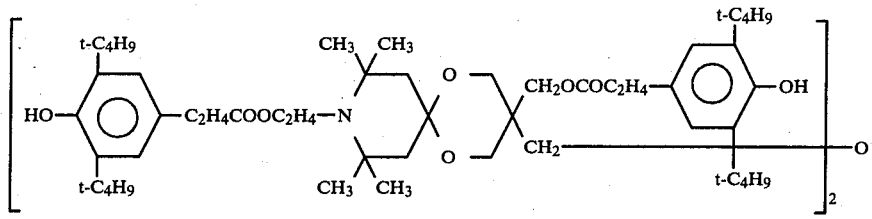

3.

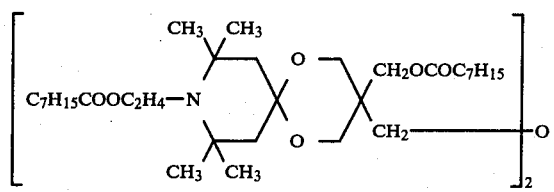

4.

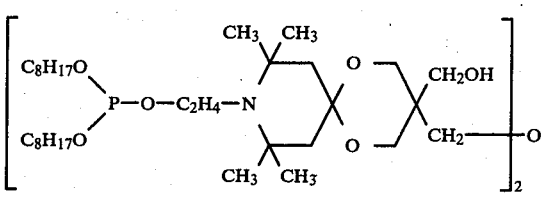

5.

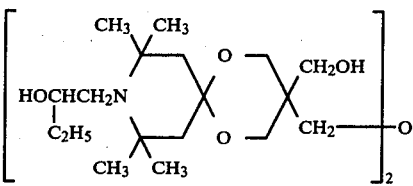

6.

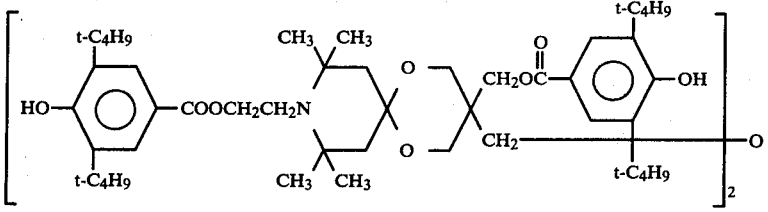

7.

-continued
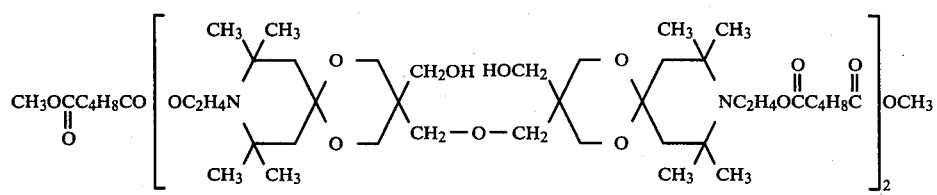 8.
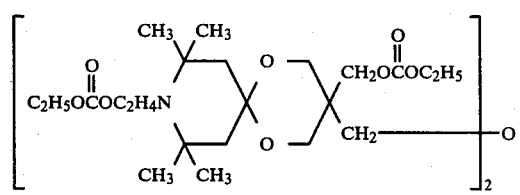 9.
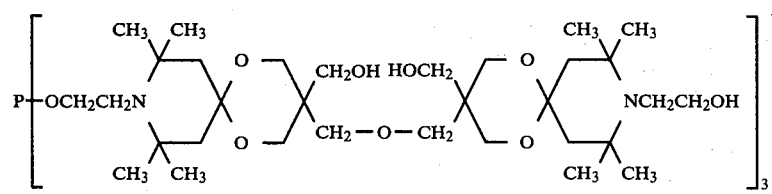 10.
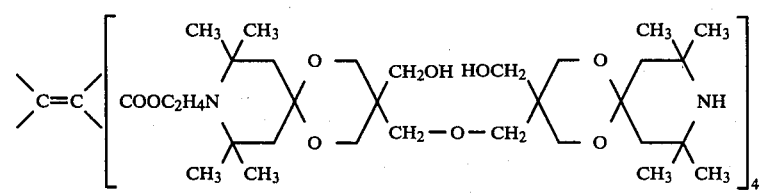 11.
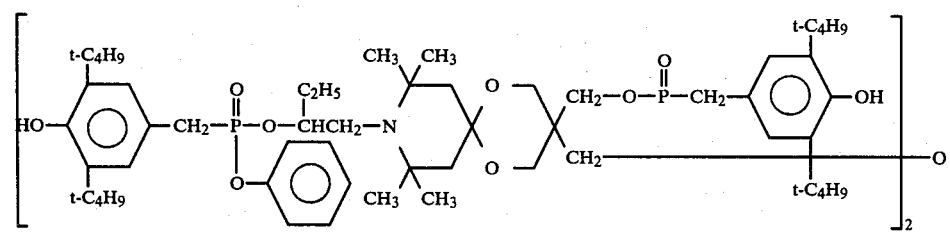 12.
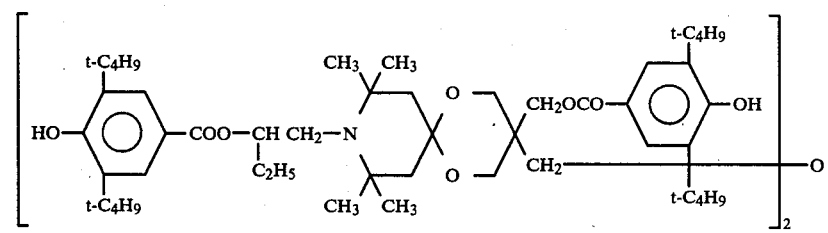 13.
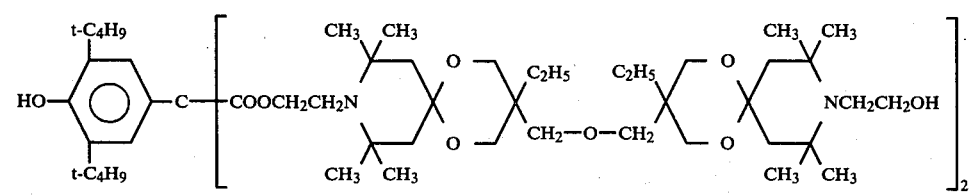 14.

15. 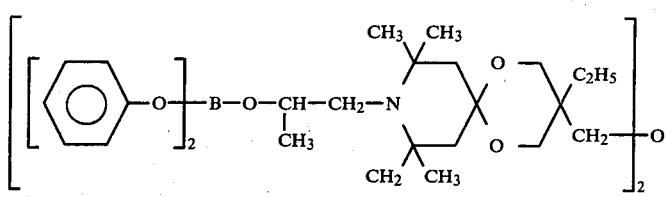
16. 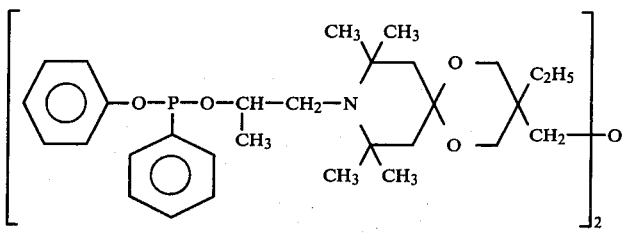
17. 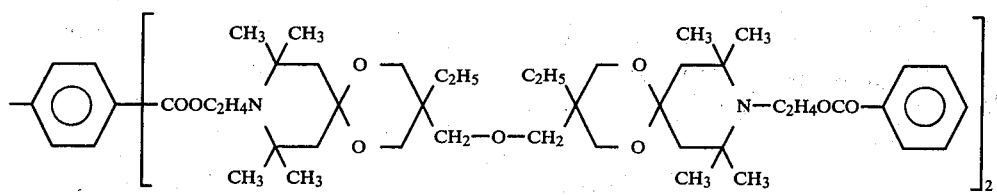
18. 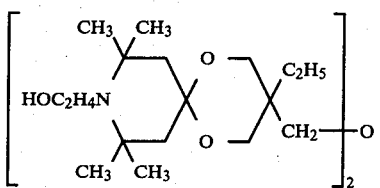
19. 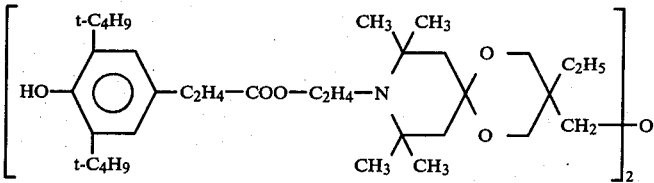
20. 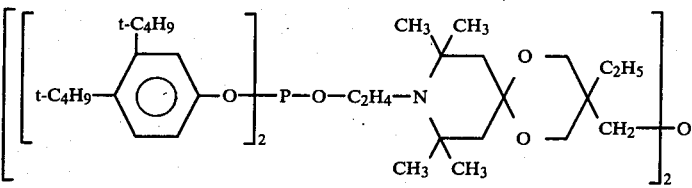
21. 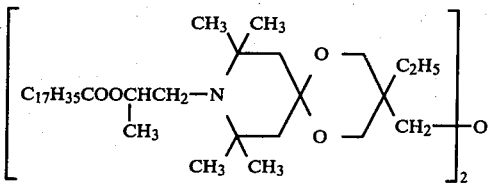
22. 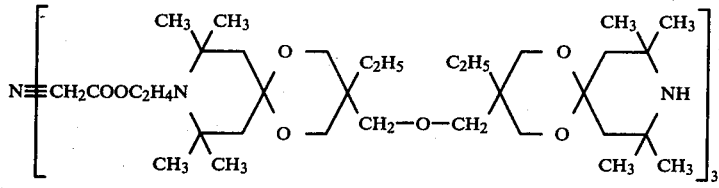

-continued
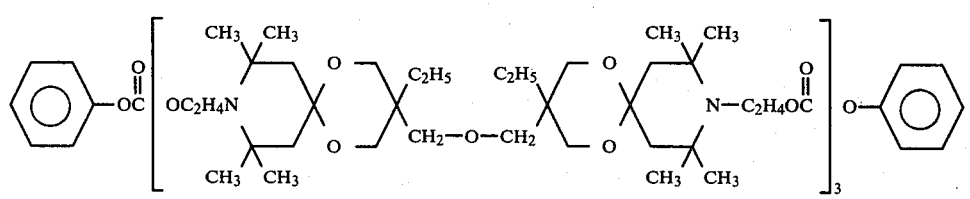
23.
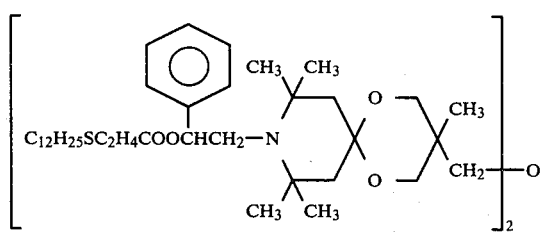
24.
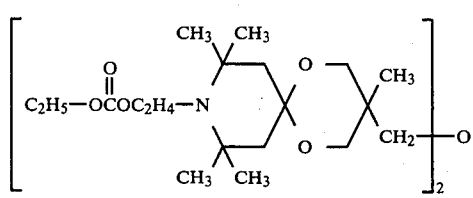
25.
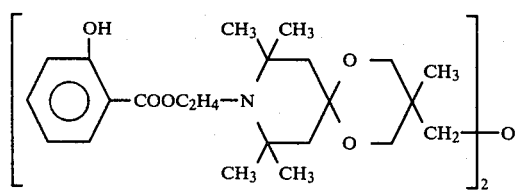
26.
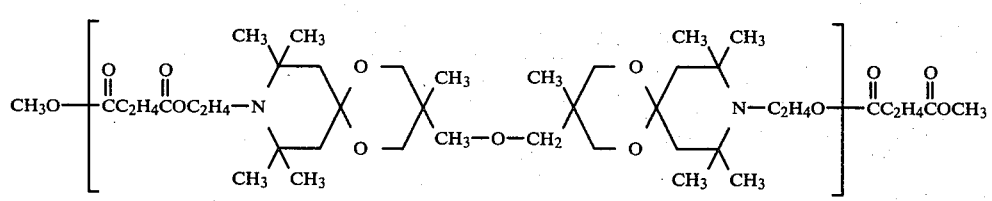
27.
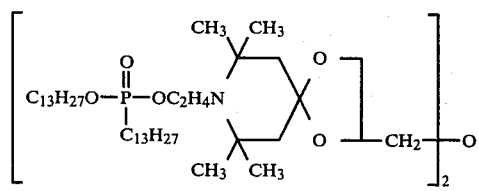
28.
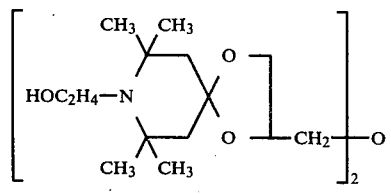
29.

-continued
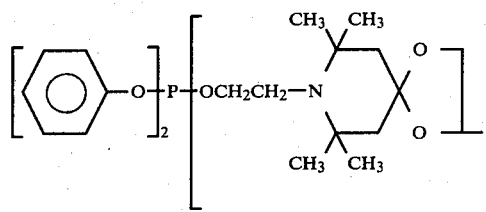 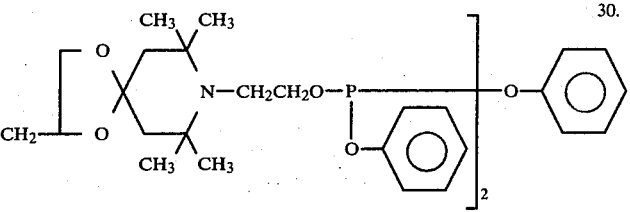
30.
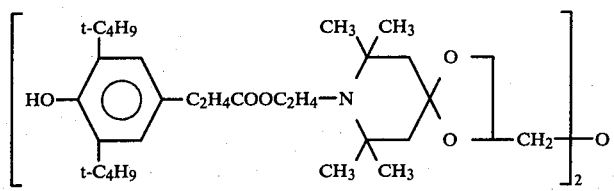
31.
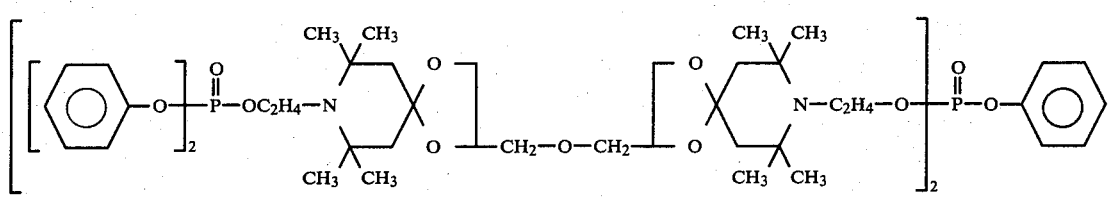
32.
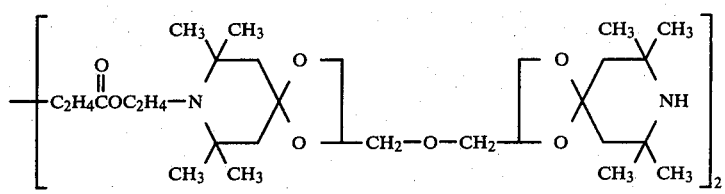
33.
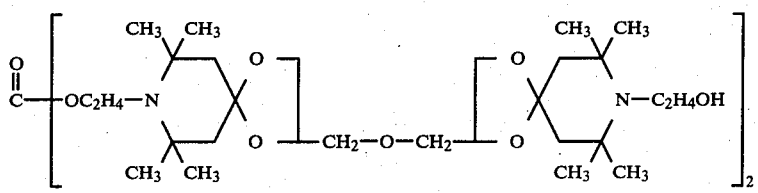
34.
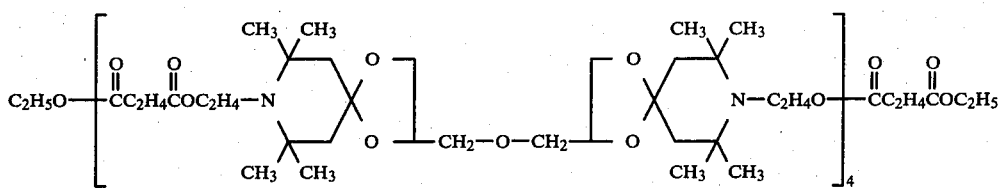
35.
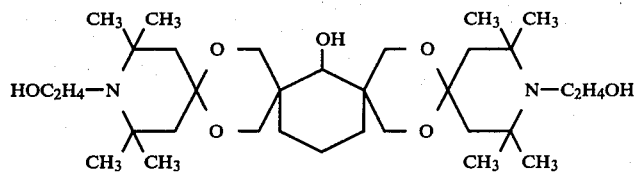
36.
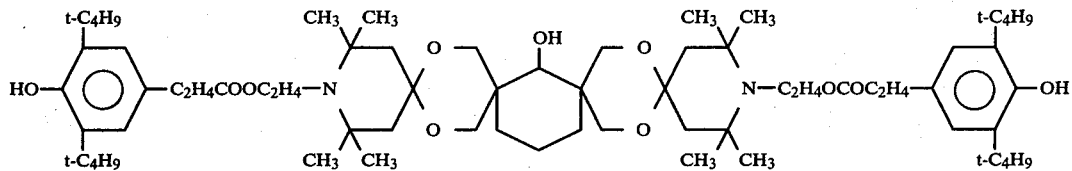
37.

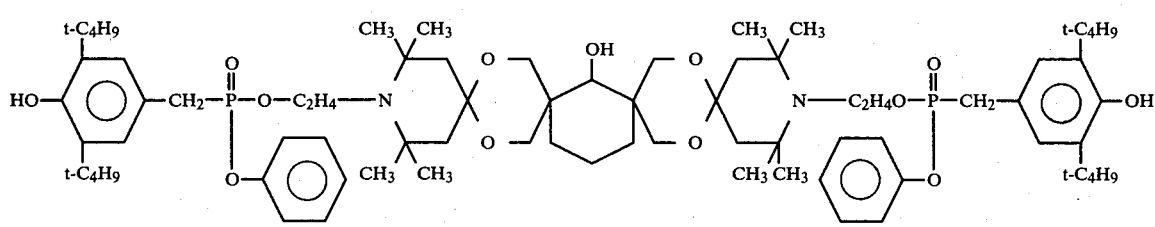
38.

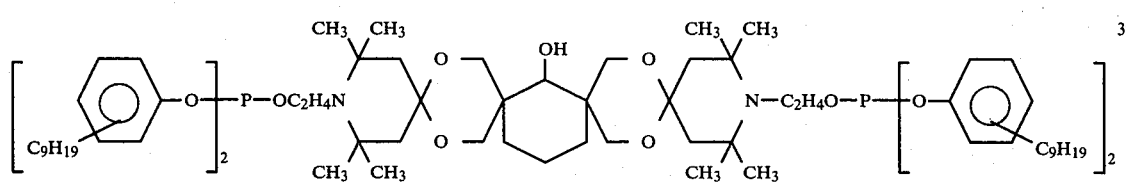
39.

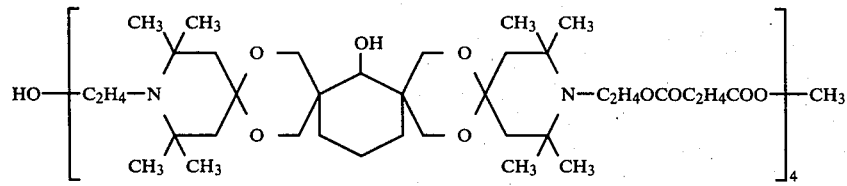
40.

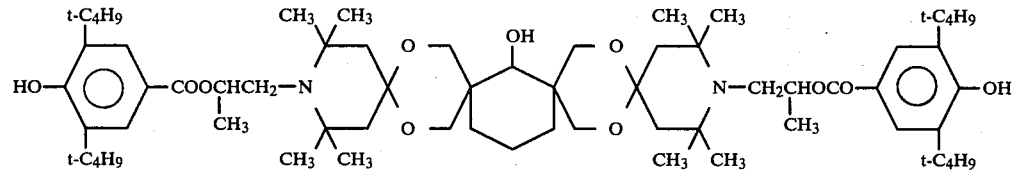
41.

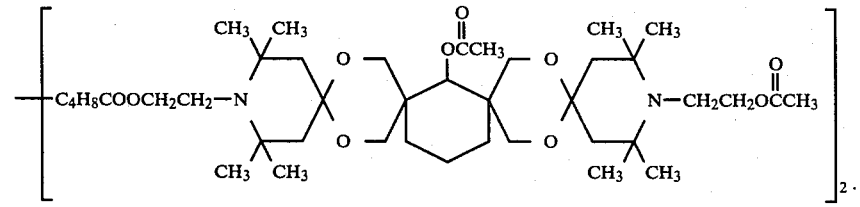
42.

Compounds having the general formula (I) of this invention are readily prepared by the reaction of the base compound:

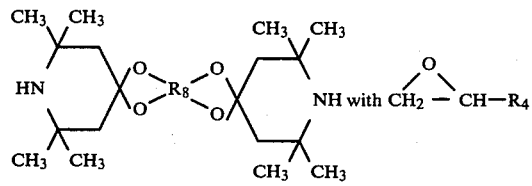

followed by esterification, if necessary.

They also can be prepared by the reaction of

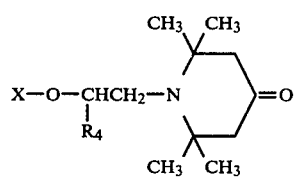

prepared beforehand with

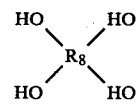

The following Examples illustrate the preparation of the exemplary compounds of the invention noted above:

EXAMPLE I

Preparation of:

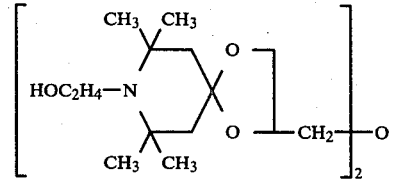

7.5 g of oxabis (8-aza-7,7,9,9-tetramethyl-1,4-dioxaspiro[4,5]-3-decylmethane) was dissolved in a mixture of water 40 ml and ethanol 30 ml, and then ethylene oxide was blown into the mixture at 25° C. The mixture was stirred for 35 hours under reflux. After solvent was distilled off, the product was dissolved in toluene and washed by water, and then the toluene was distilled off:

8.2 g of viscous pale yellow liquid was obtained.

Amine value: Calculated: 5.30%; Found: 5.41%.

EXAMPLE II

Preparation of:

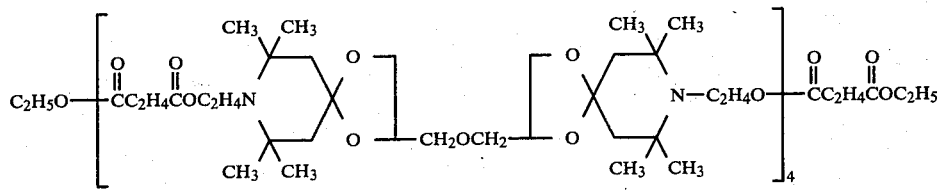

The mixture of the compound obtained in Example I, 2.64 g, diethyl succinate 1.09 g, xylene 20 ml, and lithium amide 0.04 g was reacted for nine hours under reflux. After cooling, the mixture was washed, dried and solvent was distilled off, and 3.0 g of resinous product was obtained. The molecular weight of the product, measured by the vapor pressure method, was about 2,500.

The 2,2,6,6-tetrasubstituted-4-piperidyl spiro aliphatic ethers of the invention are effective stabilizers to enhance the resistance to deterioration due to heat and/or light of synthetic polymeric materials which are susceptible to such degradation, including polyolefins such as low density polyethylene, high density polyethylene, polypropylene, polybutylene, polyisobutylene, polypentylene, and polyisopentylene; polystyrene; polydienes, such as polybutadiene and polyisoprene; and copolymers of olefins and dienes with other ethylenically and acetylenically unsaturated monomers, such as ethylene-propylene copolymers, ethylenebutene copolymers, ethylene-pentene copolymers, ethylene-vinyl acetate copolymers, styrene-butadiene copolymers, acrylonitrilestyrene-butadiene copolymers, synthetic rubbers of all types, such as polychloroprene; polyvinyl halides, including polyvinyl chloride homopolymer; polyvinylidene chloride; and copolymers of vinyl chloride and vinylidene chloride; vinyl chloride and vinyl acetate; vinylidene chloride and vinyl acetate; and other ethylenically unsaturated monomers; polyacetals such as polyoxymethylene and polyoxyethylene; polyesters such as polyethylene glycol-terephthalic acid esters polymers; polyamides such as polyepsiloncaprolactam, polyhexamethylene adipamide and polydecamethylene adipamide; polyurethanes; and epoxy resins.

The synthetic polymer can be in any physical form, including (for example) filaments, yarns, films, sheets, molded articles, latex, and foam.

The piperidyl spiro aliphatic ethers of the invention can be used as a stabilizer in an amount within the range from about 0.001 to about 10 parts by weight, preferably from 0.01 to 5 parts by weight, per 100 parts by weight of resin.

The piperidyl spiro aliphatic ethers of the invention can also be incorporated in the reaction mixture of monomers of polymerizable components used for preparation of the polymer to be stabilized, in which event the piperidyl spiro aliphatic ether can become a constituent part of the polymer molecule, and exert its stabilizing effect there. Examples are the reaction mixtures for preparation of polyaddition or polycondensation polymers such as polyurethanes and polyesters. In such cases, amounts of piperidyl spiro aliphatic ether within the range from about 0.001 to about 10 parts by weight, preferably from 0.01 to 5 parts by weight, per 100 parts by weight of total monomers or polymerizable components can be used.

The stabilizers of the invention can be employed as the sole stabilizer or, preferably, in combination with other conventional heat and light stabilizers for the particular synthetic polymer.

Thus, for example, in the case of polyvinyl chloride resins, other polyvinyl chloride resin heat stabilizers can be included, including polyvalent metal fatty acid salts such as barium and cadmium salts of the higher fatty acids; organic triphosphites; organotin compounds; hindered phenols; and epoxy compounds.

With polyolefin resins there can be employed fatty acid salts of polyvalent metals, organic phosphites, phenolic and thiophenolic antioxidants, and the higher fatty alcohol esters of thiodipropionic acids, such as, for example, dilauryl thiodipropionate.

With polyamide resin compositions, polyamide stabilizers such as copper salts in combination with iodides and/or phosphorus compounds and salts of divalent manganese can be used.

With synthetic rubbers and acrylonitrile-butadienestyrene terpolymers, antioxidants such as hindered phenols and bis-phenols, polyvalent metal salts of the higher fatty acids, and organic phosphites can be used.

In addition, other conventional additives for synthetic polymers, such as plasticizers, lubricants, emulsifiers, antistatic agents, flame-proofing agents, pigments and fillers, can be employed.

The following Examples in the opinion of the inventors represent preferred embodiments of synthetic resin compositions in accordance with the invention:

EXAMPLES 1 TO 12

A group of polyvinyl chloride resin compositions was prepared having the following formulation:

| Ingredient | Parts by Weight |
|---|---|
| Polyvinyl chloride | 100 |
| Dioctylphthalate | 48 |
| Epoxidized soybean oil | 2 |
| Tris-nonyl phenyl phosphite | 0.2 |
| Ca stearate | 1.0 |
| Zn stearate | 0.1 |
| Stabilizer as shown in Table I | 0.3 |

This formulation was blended and sheeted off on a two-roll mill to form sheets 1 mm thick. The light resistance of these sheets was then determined by placing strips 1 cm wide in a Weather-O-Meter, and exposing them to ultraviolet light. The time in hours was then noted for the sheets to develop a noticeable discoloration and/or embrittlement, indicating deterioration due to oxidation in the presence of ultraviolet light.

This test was repeated for the stabilizers in accordance with the invention, having the formulae indicated in Table I, in comparison with four controls, oxabis-(9-aza-3-ethyl-8,8,10,10-tetramethyl-1,5-dioxaspiro[5,5]-3-undecylmethane), bis-(9-aza-3-ethyl-8,8,10,10-tetramethyl-1,5-dioxaspiro[5,5]-3-undecylmethyl)carbonate, oxabis-(9-aza-3-hydroxymethyl-8,8,10,10-tetramethyl-1,5-dioxaspiro[5,5]-3-undecylmethane) and 1-(3,5-di-t-butyl-4-hydroxyphenylpropionyloxyethyl)-2,2,6,6-tetramethyl-4-piperidinyl-3,5-di-t-butyl-4-hydroxyphenylpropionate.

The following results were obtained:

TABLE I

| | Stabilizer | Hours to Failure |
|---|---|---|
| Control 1 | None | 180 |
| Control 2 | Oxabis-(9-aza-3-ethyl-8,8,10,10-tetramethyl-1,5-dioxaspiro[5,5]-3-undecylmethane) | 590 |
| Control 3 | Bis-(9-aza-3-ethyl-8,8,10,10-tetramethyl-1,5-dioxaspiro[5,5]-3-undecylmethyl)carbonate | 260 |
| Control 4 | Oxabis-(9-aza-3-hydroxymethyl-8,8,10,10-tetramethyl-1,5-dioxaspiro[5,5]-3-undecylmethane) | 600 |
| Control 5 | 1-(3,5-di-t-butyl-4-hydroxyphenylpropionyloxyethyl)-2,2,6,6-tetramethyl-4-piperidinyl-3,5-di-t-butyl-4-hydroxyphenylpropionate | 430 |
| Example No. 1 | $[HOC_2H_4-N(\text{piperidinyl-spiro-dioxane})-CH_2OH, CH_2-O]_2$ | 750 |
| 2 | $[HO-C_6H_2(t-C_4H_9)_2-C_2H_4COOC_2H_4-N(\text{piperidinyl-spiro-dioxane})-CH_2OCOC_2H_4-C_6H_2(t-C_4H_9)_2-OH, CH_2-O]_2$ | 820 |
| 3 | $CH_3OCOC_4H_8CO[OC_2H_4N(\text{piperidinyl-spiro-dioxane})-CH_2OH, HOCH_2(\text{piperidinyl-spiro-dioxane})NC_2H_4OCOC_4H_8C]_2 OCH_3$ (with $CH_2-O-CH_2$ bridge) | 840 |
| 4 | $P[OCH_2CH_2N(\text{piperidinyl-spiro-dioxane})-CH_2OH, HOCH_2(\text{piperidinyl-spiro-dioxane})NCH_2CH_2OH]_3$ (with $CH_2-O-CH_2$ bridge) | 790 |

TABLE I-continued

| Stabilizer | Hours to Failure |
|---|---|
| 5 (structure with phenyl-O-P(phenyl)-O-CH(CH₃)-CH₂-N-piperidine-spiro-dioxane with C₂H₅ and CH₂-O group)₂ | 810 |
| 6 (3,5-di-t-C₄H₉-4-HO-phenyl-C₂H₄-COO-C₂H₄-N-piperidine-spiro-dioxane with C₂H₅ and CH₂-O group)₂ | 820 |
| 7 (C₂H₅-O-C(O)-C₂H₄-N-piperidine-spiro-dioxane with CH₃ and CH₂-O group)₂ | 780 |
| 8 (PhO)₂P-OCH₂CH₂-N(piperidine)-O-CH₂OCH₂-O-(piperidine)N-CH₂CH₂O-P(OPh)₂ | 810 |
| 9 (PhO)₂P(=O)-OC₂H₄-N(piperidine)-O-CH₂-O-CH₂-O-(piperidine)N-C₂H₄-O-P(=O)-OPh | 780 |
| 10 C₂H₅O-C(=O)C₂H₄C(=O)OC₂H₄-N(piperidine)-O-CH₂-O-CH₂-O-(piperidine)N-C₂H₄O-C(=O)C₂H₄C(=O)OC₂H₅ (×4) | 850 |
| 11 (3,5-di-t-C₄H₉-4-HO-phenyl)-CH₂-P(=O)(OPh)-O-C₂H₄-N(piperidine)-O-CH₂-C(OH)-CH₂-O-(piperidine)N-C₂H₄O-P(=O)(OPh)-CH₂-(3,5-di-t-C₄H₉-4-HO-phenyl) | 830 |

TABLE I-continued

| Stabilizer | | Hours to Failure |
|---|---|---|
| 12 | HO—[C₂H₄—N(2,2,6,6-tetramethylpiperidine-O-)CH(OH)(cyclohexane with O linkages)—N(2,2,6,6-tetramethylpiperidine)—C₂H₄OCOC₂H₄COO]₄—CH₃ | 830 |

It is apparent that each of the stabilizers in accordance with the invention is far superior to the Controls.

EXAMPLES 13 TO 26

Polypropylene compositions were prepared using stabilizers of the invention and of the prior art, and having the following formulation:

| Ingredient | Parts by Weight |
|---|---|
| Polypropylene | 100 |
| Stearyl β-3,5-di-tert-butyl-4-hydroxyphenyl propionate | 0.2 |
| Stabilizer as shown in Table II | 0.3 |

The compositions were thoroughly blended in a Brabender Plastograph, and then compression-molded to form sheets 0.3 mm thick. Pieces 2.5 cm² were cut off from the sheets and exposed to a high pressure mercury lamp with and without immersion in hot water at 80° C. for fifteen hours. The hours to failure were noted in comparison with four prior art stabilizers, and the results are shown in Table II.

TABLE II

| | Stabilizer | Hours to Failure Without Immersion | Hours to Failure After Immersion for 15 hours |
|---|---|---|---|
| Control 1 | Oxabis-(9-aza-3-hydroxymethyl-8,8,10,10-tetramethyl-1,5-dioxaspiro[5,5]-3-undecylmethane) | 620 | 520 |
| Control 2 | 9-Aza-3-ethyl-8,8,10,10-tetramethyl-1,5-dioxaspiro[5,5]-3-undecylmethyl-3-(3,5-di-t-butyl-4-hydroxyphenyl)propionate | 610 | 500 |
| Control 3 | Bis-(2,2,6,6-tetramethyl-4-piperidinyl)sebacate | 490 | 340 |
| Control 4 | Oxabis-(8-aza-7,7,9,9-tetramethyl-1,4-dioxaspiro[4,5]-2-decylmethane) | 605 | 515 |
| Example No. | | | |
| 13 | [HO—(2,6-di-t-butylphenyl)—C₂H₄COOC₂H₄—N(2,2,6,6-tetramethylpiperidine)—CH₂OCOC₂H₄—(3,5-di-t-butyl-4-hydroxyphenyl)—OH / CH₂—O]₂ | 780 | 700 |
| 14 | [C₈H₁₇O)₂P—O—C₂H₄—N(2,2,6,6-tetramethylpiperidine)—CH₂OH / CH₂—O]₂ | 750 | 680 |
| 15 | | 810 | 730 |

TABLE II-continued
| Stabilizer | Hours to Failure | |
| --- | --- | --- |
| | Without Immersion | After Immersion for 15 hours |
| 16 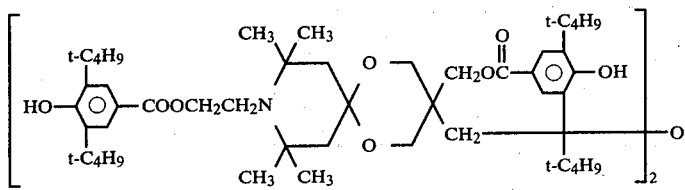 | 800 | 730 |
| 17 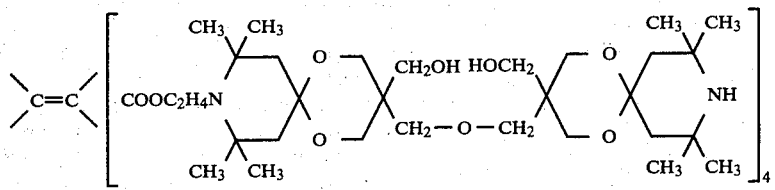 | 780 | 710 |
| 18 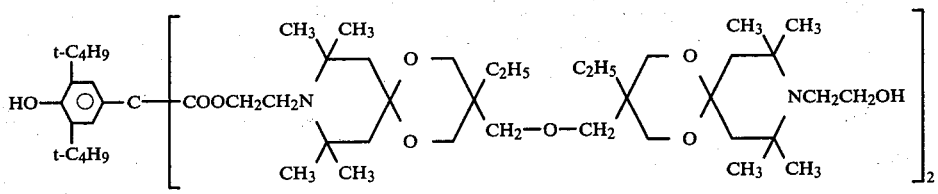 | 720 | 640 |
| 19 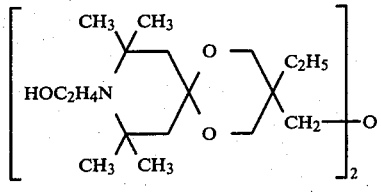 | 810 | 740 |
| 20 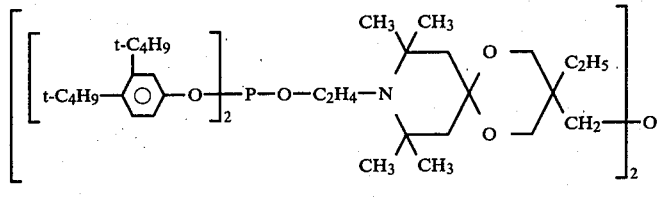 | 800 | 740 |
| 21 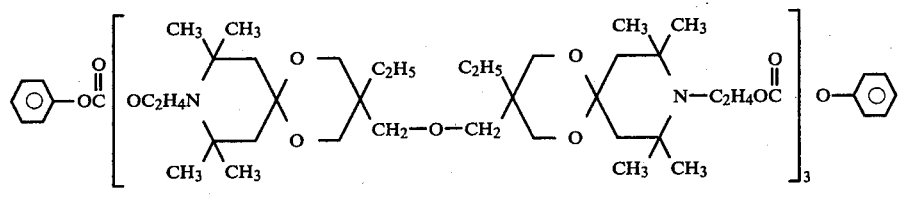 | 770 | 720 |

TABLE II-continued

| Stabilizer | Hours to Failure | |
|---|---|---|
| | Without Immersion | After Immersion for 15 hours |
| 22 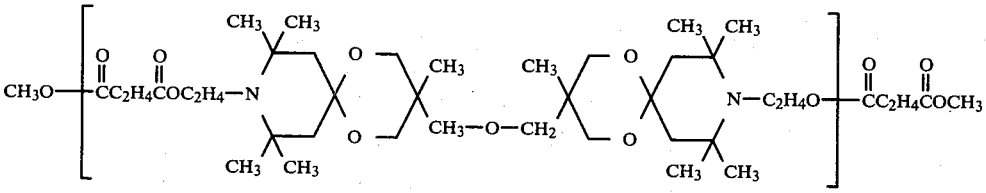 | 730 | 670 |
| 23 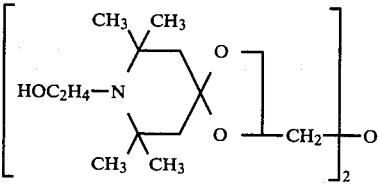 | 770 | 700 |
| 24 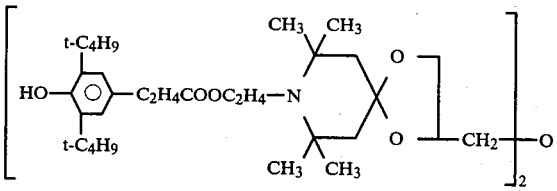 | 760 | 700 |
| 25 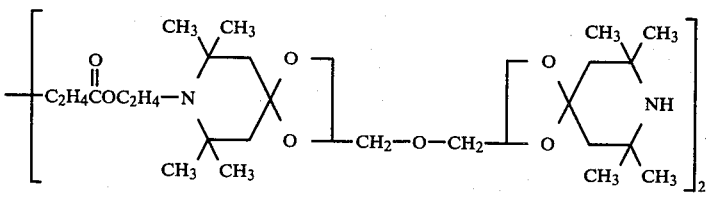 | 740 | 670 |
| 26 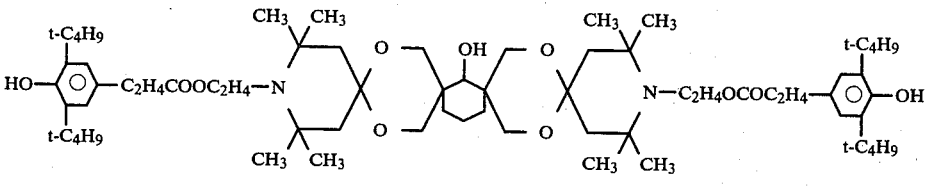 | 750 | 670 |

It is apparent that each of the stabilizers in accordance with the invention is far superior to the Controls.

EXAMPLES 27 TO 40

Ethylene-vinyl acetate copolymer compositions were prepared using stabilizers of the invention and of the prior art, and having the following formulation:

| Ingredient | Parts by Weight |
|---|---|
| Ethylene-vinyl acetate copolymer | 100 |
| 2,6-di-t-butyl-p-cresol | 0.1 |
| Ca stearate | 0.1 |
| Zn stearate | 0.1 |
| Diisodecylphenyl phosphite | 0.2 |
| Stabilizer as shown in Table III | 0.2 |

The stabilizer was blended with the polymer on a two-roll mill at 130° C., and sheets 0.4 mm thick were then compression-molded at 140° C. from the resulting blend. Pieces 2.5 cm² were cut off from the sheets and exposed to ultraviolet light in a Weather-O-Meter for 500 hours. At the start and at the conclusion of the test, tensile strength of the sheet samples was determined.

The results in comparison with four controls, oxabis-(9-aza-3-hydroxymethyl-8,8,10,10-tetramethyl-1,5-dioxaspiro-[5,5]-3-undecylmethane), bis-(2,2,6,6-tetramethyl-4-piperidinyl)succinate, oxabis-(9-aza-3-ethyl-8,8,10,10-tetramethyl-1,5-dioxaspiro-[5,5]-3-undecylmethane) and condensed compound of 1-hydroxyethyl-2,2,6,6-tetramethyl-4-piperidinol with dimethyl succinate (molecular weight >2,000) are given in Table III as percent retention of the initially determined tensile strength:

TABLE III

| | Stabilizer | % Retention of Tensile Strength After 500 Hours |
|---|---|---|
| Control 1 | Oxabis-(9-aza-3-hydroxy-methyl-8,8,10,10-tetramethyl-1,5-dioxaspiro-[5,5]-3-undecylmethane) | 70 |
| Control 2 | Bis-(2,2,6,6-tetramethyl-4-piperidinyl)succinate | 62 |
| Control 3 | Oxabis-(9-aza-3-ethyl-8,8,10,10-tetramethyl-1,5-dioxaspiro[5,5]-3-undecylmethane) | 68 |
| Control 4 | Condensed compound of 1-hydroxy-ethyl-2,2,6,6-tetramethyl-4-piperdinol with dimethyl succinate (Molecular weight 2,000) | 65 |
| Example No. | | |
| 27 | | 76 |
| 28 | | 80 |
| 29 | | 83 |
| 30 | | 84 |

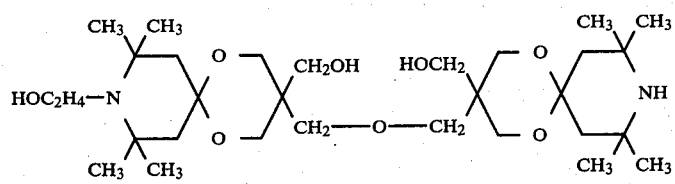

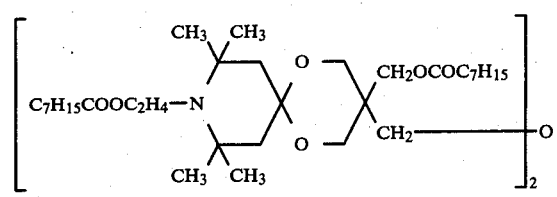

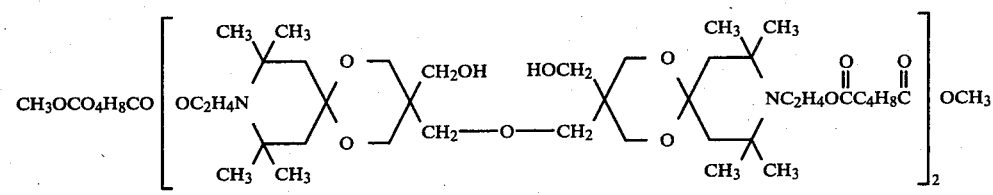

TABLE III-continued
| | Stabilizer | % Retention of Tensile Strength After 500 Hours |
|---|---|---|
| 31 | 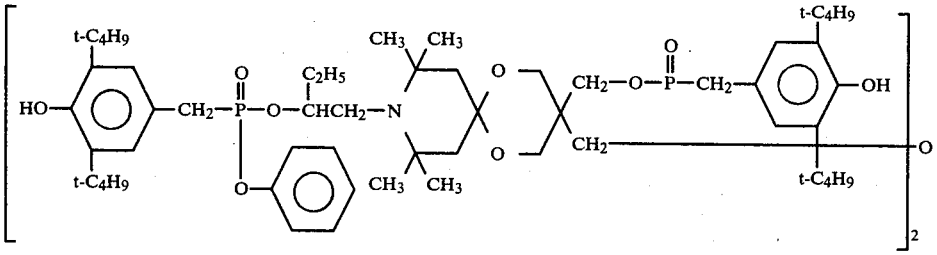 | 75 |
| 32 | 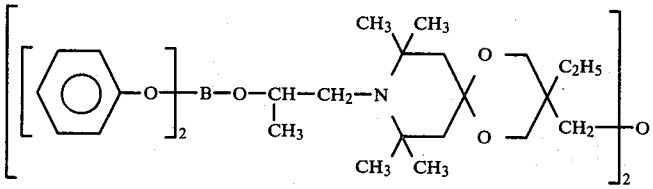 | 82 |
| 33 | 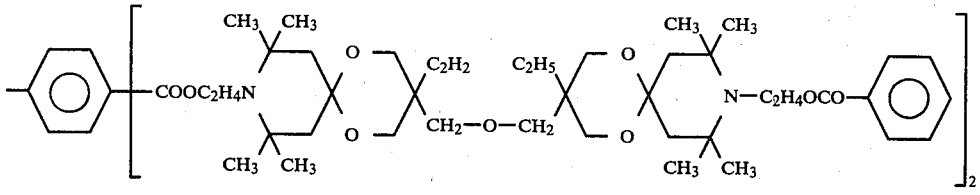 | 79 |
| 34 | 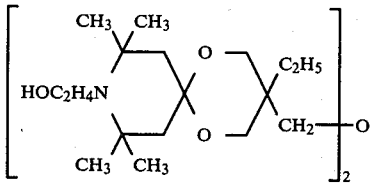 | 79 |
| 35 | 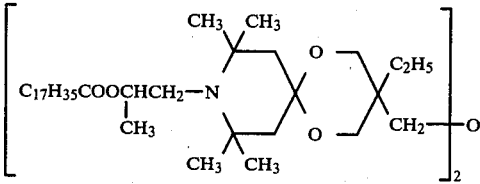 | 78 |
| 36 | 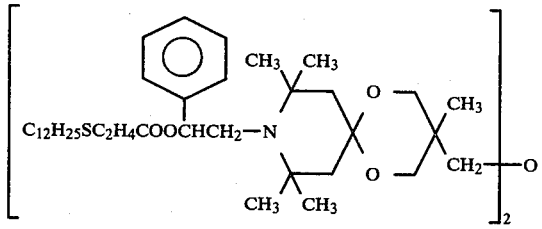 | 83 |

TABLE III-continued

| Stabilizer | % Retention of Tensile Strength After 500 Hours |
|---|---|
| 37 | 78 |
| 38 | 80 |
| 39 | 82 |
| 40 | 79 |

It is apparent that each of the stabilizers in accordance with the invention is far superior to the Controls.

EXAMPLES 41 TO 53

High density polyethylene compositions were prepared using the stabilizers of the invention and of the prior art, and having the following formulation:

| Ingredient | Parts by Weight |
|---|---|
| High-density polyethylene | 100 |
| Ca stearate | 1 |
| Tetrakis-(methylene-3-(3,5-di-t-butyl-4-hydroxyphenyl)propionate)methane | 0.1 |
| Distearylthiodipropionate | 0.3 |
| Stabilizer as shown in Table IV | 0.2 |

The stabilizer was blended with the polymer on a two-roll mill and sheets 0.5 mm thick were prepared by compression-molding of the blend. Pieces 2.5 cm$^2$ were cut off from the sheets, and exposed in a Weather-O-Meter to ultraviolet light. The time in hours when degradation set in, as determined by a significant discoloration and/or embrittlement, was noted as hours to failure, and the results are reported in Table IV.

TABLE IV
| | Stabilizer | Hours to Failure |
|---|---|---|
| Control 1 | Oxabis-(9-aza-3-ethyl-8,8,10,10-tetramethyl-1,5-dioxaspiro[5,5]-3-undecylmethane) | 870 |
| Control 2 | Tris-(9-aza-3-ethyl-8,8,10,10-tetramethyl-1,5-dioxaspiro[5,5]-3-undecylmethyl)phosphite | 900 |
| Control 3 | 2,2,4,4,18,18,20,20-Octamethyl-3,19-diaza-7,15,22,26-tetraoxa-24-hydroxy tetraspiro[5,2,3,2,5,2,1,2]-hexaeicosane | 860 |
| Control 4 | Bis-(2,2,6,6-tetramethyl-4-piperidinyl)adipate | 680 |
| Example No. | | |
| 41 | 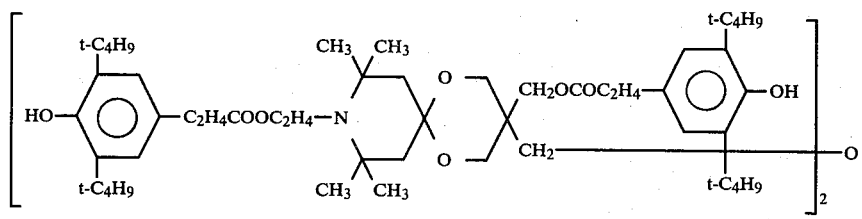 | 1150 |
| 42 | 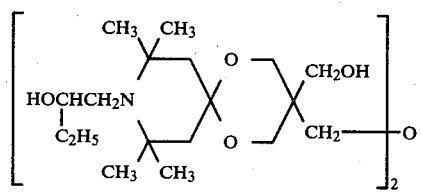 | 1050 |
| 43 | 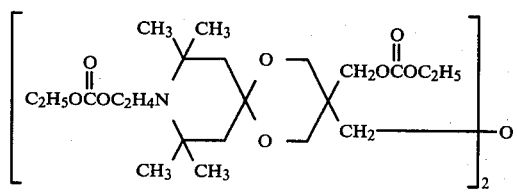 | 1060 |
| 44 | 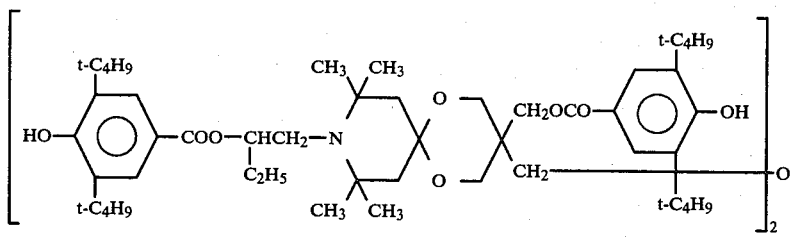 | 1090 |
| 45 | 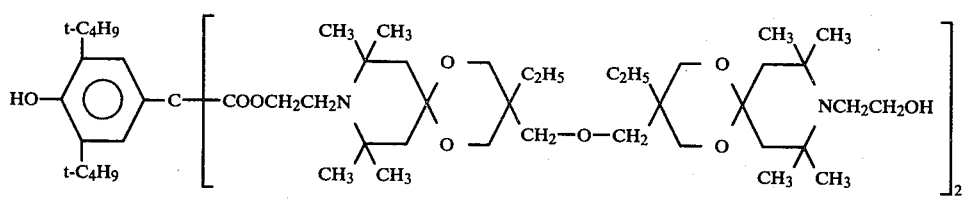 | 1170 |
| 46 | | 1200 |

TABLE IV-continued
| Stabilizer | Hours to Failure |
|---|---|
| 47 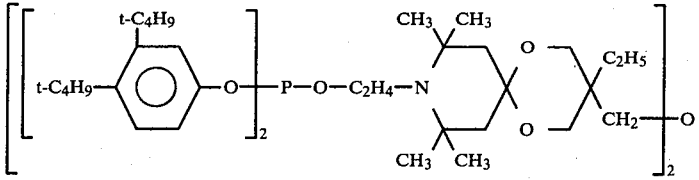 | 1140 |
| 48 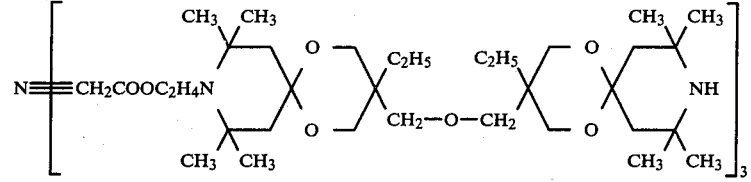 | 1100 |
| 49 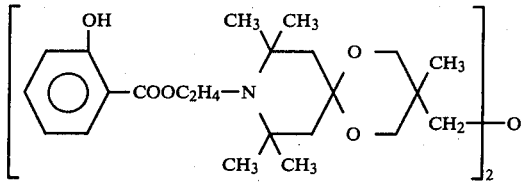 | 1070 |
| 50 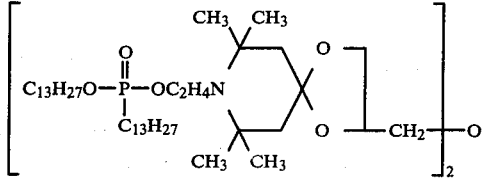 | 1150 |
| 51 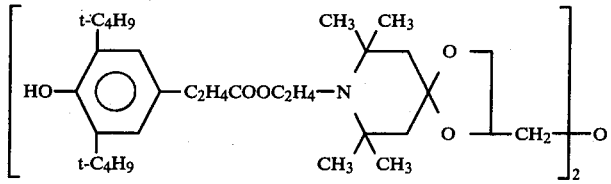 | 1040 |
| 52 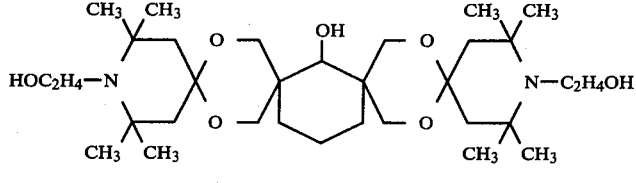 | 1180 |

TABLE IV-continued

| Stabilizer | Hours to Failure |
|---|---|
| 53: HO-C6H3(t-C4H9)2-C2H4COOC2H4-N(piperidine-tetramethyl)-CH2-O-C6H9(OH)-O-CH2-(piperidine-tetramethyl)N-C2H4OCOC2H4-C6H3(t-C4H9)2-OH | 1120 |
| [C9H19-C6H4-O-P(-OC2H4N(piperidine-tetramethyl)-CH2-O-)2-C6H9(OH)-(-O-CH2-(piperidine-tetramethyl)N-C2H4O-P-O-C6H4-C9H19)]2 |  |

It is apparent that each of the stabilizers in accordance with the invention is far superior to the Controls.

EXAMPLES 54 TO 66

Acrylonitrile-butadiene-styrene terpolymer resin compositions were prepared using stabilizers of the invention and of the prior art, and having the following formulation:

| Ingredient | Parts by Weight |
|---|---|
| Acrylonitrile-butadiene-styrene terpolymer | 100 |
| 4,4'-Butylidene-bis-(2-tert-butyl-m-cresol) | 0.1 |
| Stabilizer as shown in Table V | 0.3 |

The stabilizer was blended with the resin on a two-roll mill, and sheets 3 mm thick were prepared by compression-molding of the resulting blend. Pieces 2.5 cm$^2$ were cut off from the sheets, and subjected to ultraviolet light in a Weather-O-Meter for 800 hours. Tensile strength before and after the test exposure was determined, and the results reported as the percent of tensile strength retained, at the end of this time, in Table V.

TABLE V

| | Stabilizer | % Tensile Strength Retained |
|---|---|---|
| Control 1 | Oxabis-(9-aza-3-hydroxymethyl-8,8,10,10-tetramethyl-1,5-dioxaspiro[5,5]-3-undecylmethane) | 65 |
| Control 2 | 2(2'-Hydroxy-5'-methylphenyl)benzotriazole | 63 |
| Control 3 | Bis-(9-aza-3-ethyl-8,8,10,10-tetramethyl-1,5-dioxaspiro[5,5]-3-undecylmethyl)carbonate | 62 |
| Control 4 | 3,15-Bis-(2-hydroxyethyl)2,2,4,4,14,14,16,16-octamethyl-3,15-diaza-7,11,18,21-tetraoxatrispiro-[5,2,2,5,2,2]heneicosane | 66 |
| Example No. | | |
| 54 | [HOC2H4-N(piperidine-tetramethyl)-CH2-O-C(CH2OH)(CH2-)-O-]2 | 82 |

TABLE V-continued

| Stabilizer | % Tensile Strength Retained |
|---|---|
| 55 (structure: bis[dioctyl phosphite-ethyl-tetramethylpiperidine-spiro-dioxane with CH₂OH] ) | 83 |
| 56 (structure: bis[ethoxycarbonyl-ethyl-tetramethylpiperidine-spiro-dioxane with CH₂OCOC₂H₅] ) | 86 |
| 57 (structure: bis[di-t-butyl-hydroxybenzyl phosphonate phenyl ester-ethyl-tetramethylpiperidine-spiro-dioxane with phosphonate-di-t-butylphenol] ) | 89 |
| 58 (structure: bis[tolyl-COOC₂H₄N-tetramethylpiperidine-spiro-dioxane-CH₂OCH₂ linker-spiro-dioxane-tetramethylpiperidine-N-C₂H₄OCO-phenyl] ) | 84 |
| 59 (structure: bis[di-t-butyl-hydroxyphenyl-C₂H₄-COO-C₂H₄-N-tetramethylpiperidine-spiro-dioxane] ) | 90 |
| 60 (structure: tris[phenyl-OC(O)-C₂H₄N-tetramethylpiperidine-spiro-dioxane-CH₂OCH₂-spiro-dioxane-tetramethylpiperidine-N-C₂H₄OC(O)-phenyl] ) | 85 |
| 61 (structure: bis[HOC₂H₄-N-tetramethylpiperidine-spiro-dioxane-CH₂-O] ) | 82 |

TABLE V-continued

| Stabilizer | % Tensile Strength Retained |
|---|---|
| 62 [structure] | 83 |
| 63 [structure] | 84 |
| 64 [structure] | 88 |
| 65 [structure] | 85 |
| 66 [structure] | 82 |

It is apparent that each of the stabilizers in accordance with the invention is far superior to the Controls.

EXAMPLES 67 to 77

Conventional heat stabilizers for polymeric materials may lose their effectiveness because of volatilization or decomposition at high polymer processing temperatures. This is not true of the stabilizers of the invention, as shown by observing the effect of heat in repeated extrusions of ethylene-propylene copolymer compositions. These compositions were prepared using stabilizers of the invention and of the prior art, and having the following formulation:

| Ingredient | Parts by Weight |
|---|---|
| Ethylene-propylene copolymer | 100 |
| Ca stearate | 0.2 |
| Stearyl-β-(3,5-di-t-butyl-4-hydroxyphenyl) propionate | 0.1 |
| Dilauryl thiodipropionate | 0.2 |
| Stabilizer as shown in Table VI | 0.2 |

The ingredients were mixed and the compositions then extruded (cylinder temperature 230° C. and 240° C., head die temperature 250° C., velocity 20 rpm) five times. Test pieces were then molded by injection molding at 250° C. The test pieces were exposed to a high voltage mercury lamp, and the hours to failure noted as shown in Table VI. The surface of the test pieces was also noted after exposure for 300 hours.

TABLE VI

| | Stabilizer | Hours to Failure | | Surface of test pieces after exposure for 500 hours |
| --- | --- | --- | --- | --- |
| | | Extruded 1 time | Extruded 5 times | |
| Control 1 | Bis-(9-aza-8,8,10,10-tetramethyl-3-ethyl-1,5-dioxaspiro[5,5]-3-undecylmethyl)adipate | 400 | 260 | Bloom |
| Control 2 | Bis-(9-aza-3-ethyl-8,8,10,10-tetramethyl-1,5-dioxaspiro[5,5]-3-undecylmethyl)carbonate | 380 | 250 | White spots |
| Control 3 | Oxabis-(9-aza-8,8,10,10-tetramethyl-3-hydroxymethyl-1,5-dioxaspiro[5,5]-3-undecylmethane) | 490 | 380 | White spots |
| Example No. | | | | |
| 67 | | 600 | 550 | No change |
| 68 | | 640 | 580 | No change |
| 69 | | 570 | 500 | No change |
| 70 | | 630 | 550 | No change |
| 71 | | 580 | 500 | No change |
| 72 | | 610 | 540 | No change |

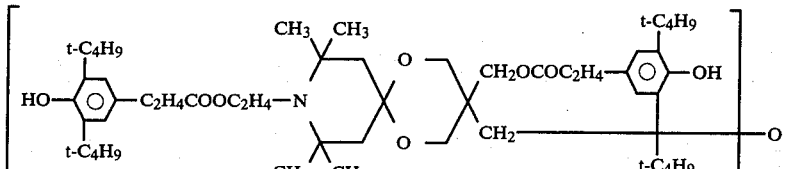

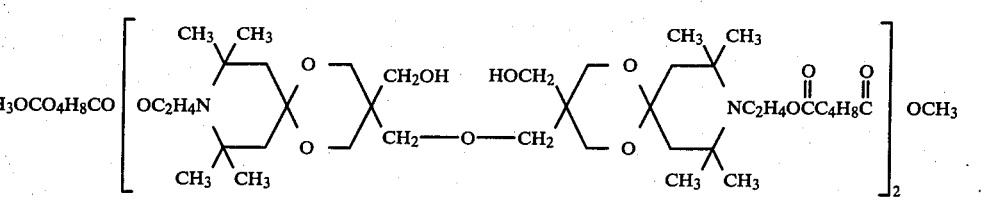

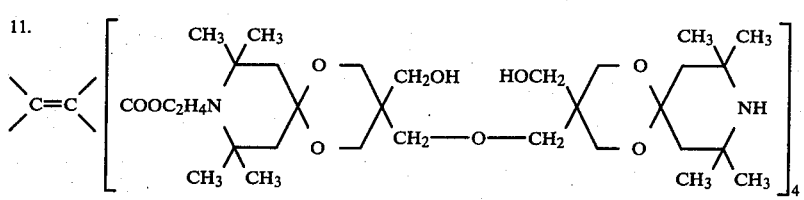

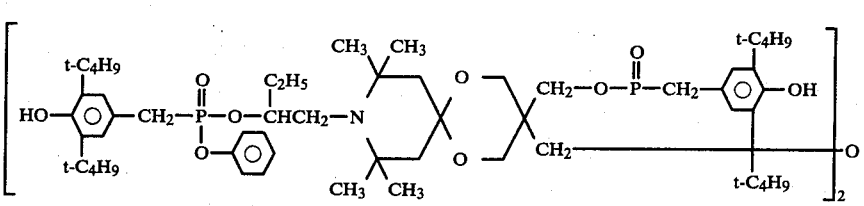

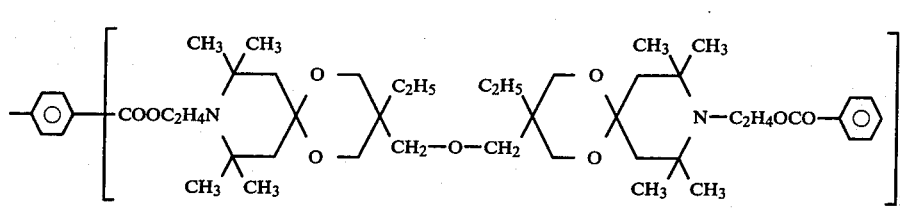

TABLE VI-continued

| Stabilizer | Hours to Failure | | Surface of test pieces after exposure for 500 hours |
|---|---|---|---|
| | Extruded 1 time | Extruded 5 times | |
| 73 [structure] | 570 | 510 | No change |
| 74 [structure] | 610 | 580 | No change |
| 75 [structure] | 590 | 520 | No change |
| 76 [structure] | 630 | 570 | No change |
| 77 [structure] | 620 | 570 | No change |

The results show that substantial amounts of the Control stabilizers are lost by volatilization, after five extrusions, while the stabilizers of the invention are substantially retained in the polymer composition.

EXAMPLES 78 to 87

Polyurethane resin compositions were prepared using stabilizers of the invention and stabilizers of the prior art, and having the following formulation:

| Ingredient | Parts by Weight |
|---|---|
| Polyurethane resin (Asahi Denka U-100)[1] | 100 |
| Ca stearate | 0.7 |
| Zn stearate | 0.3 |
| 2,6-di-t-butyl-p-cresol | 0.1 |
| Stabilizer as shown in Table VII | 0.3 |

[1] A polyurethane-isocyanurate made from toluene diisocyanate and alkylene polyol.

The stabilizer was blended with the finely powdered polyurethane resin on a two-roll mill for five minutes at 70° C., and the sheet was then compression-molded at 120° C. for five minutes to form sheets 0.5 mm thick. Pieces 2.5 cm² were cut out from the sheets, and exposed to ultraviolet light in a Weather-O-Meter for thirty hours. Elongation before and after exposure was determined, and the percent elongation retained after the exposure is given in Table VII.

TABLE VII

| | Stabilizer | % Elongation Retention |
|---|---|---|
| Control 1 | Bis-(9-aza-3-ethyl-8,8,10,10-tetramethyl-1,5-dioxaspiro[5,5]-3-undecylmethyl)adipate | 58 |
| Control 2 | Bis-(2,2,6,6-tetramethyl-4-piperidinyl)-1,6-hexamethylene dicarbamate | 55 |
| Control 3 | Oxabis-(9-aza-3-hydroxymethyl-8,8,10,10-tetramethyl-1,5-dioxaspiro[5,5]-3-undecylmethane) | 64 |
| Control 4 | 9-Aza-9-(3,5-di-t-butyl-4-hydroxyphenylpropionyloxy)ethyl-3-ethyl-8,8,10,10-tetramethyl-1,5-dioxaspiro[5,5]-3-undecylmethyl-3,5-di-t-butyl-4-hydroxyphenylpropionate | 60 |

| Example No. | Stabilizer | % Elongation Retention |
|---|---|---|
| 78 | HOC₂H₄—N[spiro structure]—CH₂OH—CH₂—O—CH₂—[spiro structure]—NH | 74 |
| 79 | [C₇H₁₅COOC₂H₄—N[spiro structure]—CH₂OCOC₇H₁₅—CH₂—]₂O | 77 |
| 80 | CH₃OCO C₄H₈CO[OC₂H₄N[spiro structure]—CH₂OH—CH₂—O—CH₂—[spiro structure]—NC₂H₄OCC₄H₈C(=O)(=O)]₂OCH₃ | 79 |
| 81 | P—[OCH₂CH₂N[spiro structure]—CH₂OH—CH₂—O—CH₂—[spiro structure]—NCH₂CH₂OH]₃ | 76 |

TABLE VII-continued

| | Stabilizer | % Elongation Retention |
|---|---|---|
| 82 | | 80 |
| 83 | | 77 |
| 84 | | 74 |
| 85 | | 73 |
| 86 | | 76 |
| 87 | | 78 |

The stabilizers of the invention are clearly superior to the Controls in enhancing resistance of the polyurethane resin to degradation under ultraviolet light.

Having regard to the foregoing disclosure, the following is claimed as the inventive and patentable embodiments thereof:

1. A compound having the formula:

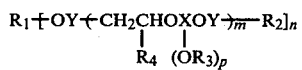

wherein:

Y is

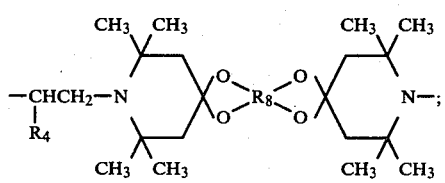

X is selected from the group consisting of alkylene having from one to about eighteen carbon atoms; cycloalkylene having from three to about eight carbon atoms; phenylene and biphenylene which when substituted with $OR_3$ have up to about eighteen carbon atoms; polyacyl

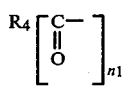

wherein $n_1$ is a number from 2 to 4; polycarbamoyl

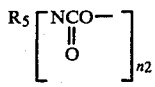

wherein $n_2$ is a number from 2 to 4;

and di- and trivalent phosphorous acid, phosphoric acid, phosphonous acid, phosphonic acid, boric acid and silicic acid groups;

$R_1$ is selected from the group consisting of hydrogen,

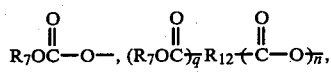

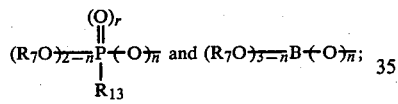

$R_2$ is selected from the group consisting of hydrogen and

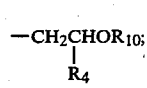

$R_3$ is selected from the group consisting of alkyl having from one to about eighteen carbon atoms; cycloalkyl having from three to about eight carbon atoms; phenyl; alkylphenyl having from about seven to about eighteen carbon atoms; and —X—O—$R_1$;

$R_4$ is selected from the group consisting of hydrogen; alkyl having from one to about eighteen carbon atoms; cycloalkyl having from three to about eight carbon atoms; phenyl; and alkylphenyl having from seven to about eighteen carbon atoms;

$R_5$ is selected from the group consisting of alkyl having from one to about eighteen carbon atoms; cycloalkyl having from three to about eight carbon atoms; phenyl; alkylphenyl having from seven to about eighteen carbon atoms;

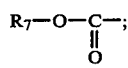

and monovalent phosphorous acid, phosphoric acid, phosphonous acid, phosphonic acid, boric acid and silicic acid groups;

$R_7$ is selected from the group consisting of alkyl having from one to about eighteen carbon atoms; phenyl; alkylphenyl and cycloalkylphenyl having up to about fifty carbon atoms;

$R_8$ is selected from the group consisting of

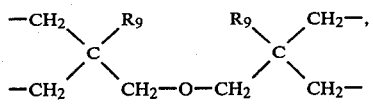

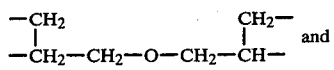

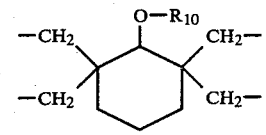

$R_9$ is selected from the group consisting of alkyl having from one to about eighteen carbon atoms; cycloalkyl having from three to about eight carbon atoms; and —$CH_2OR_{10}$;

$R_{10}$ is selected from the group consisting of hydrogen,

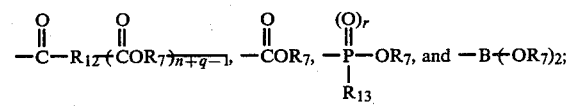

$R_{11}$ is selected from the group consisting of alkylene and oxyalkylene having from two to about ten carbon atoms and from zero to about five oxyether groups; cycloalkylene having from three to about eight carbon atoms; and phenylene, alkylphenylene, and bis(phenylene) and bis(alkylphenylene) having the phenylene linked by a member selected from the group consisting of oxo, thio, alkylene having from one to nine carbon atoms, alkylidene having from three to four carbon atoms, cyclohexylidene and benzylidene; and isocyanurate;

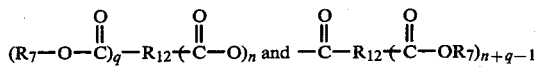

from the group consisting of $R_7$ esters having q or $n+q-1$ $R_7$ ester groups of mono-, di-, tri- or tetracarboxylic acids selected from the group consisting of aliphatic mono, di, tri and tetracarboxylic acids having from one to about eighteen carbon atoms and such acids substituted with a group selected from hydroxyl, keto, amino, imino, mercapto and alkyl hydroxy phenyl groups; benzoic acid; toluic acid; benzoic acid substituted with a group selected from alkyl and hydroxyl groups; trimellitic acid; nicotinic acid; isonicotinic acid; 2,2,6,6-tetramethyl piperidine-4-carboxylic acid, 3,8,8,10,10-pentamethyl-9-aza-1,5-dioxaspiro-[5,5]-undecane-3-carboxylic acids; phthalic acid; tetrahydrophthalic acid; isophthalic acid; terephthalic acid; endomethylene tetrahydrophthalic acid; thiophene dicarboxylic acid; furane dicarboxylic acid; and dicarboxyethyl piperidine;

$R_{13}$ is selected from the group consisting of hydrogen, $R_5$, and —O—$R_5$;
m is a number from zero to 10;
n is a number from zero to 4;
p is zero or 1;
q is a number from zero to 3; and
r is zero or 1.

2. A compound according to claim 1 in which $R_8$ is

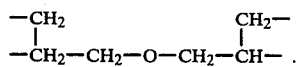

3. 2,2,6,6-Tetramethyl-4-piperidyl spiro aliphatic ethers according to claim 1 in which $R_8$ is

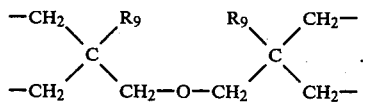

4. 2,2,6,6-Tetramethyl-4-piperidyl spiro aliphatic ethers according to claim 1 in which $R_8$ is

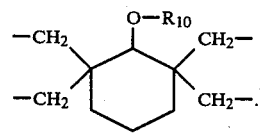

5. 2,2,6,6-Tetramethyl-4-piperidyl spiro aliphatic ethers according to claim 1 in which $R_4$ is hydrogen.

6. 2,2,6,6-Tetramethyl-4-piperidyl spiro aliphatic ethers according to claim 1 in which $R_4$ is alkyl.

7. 2,2,6,6-Tetramethyl-4-piperidyl spiro aliphatic ethers according to claim 1 in which X is alkylene.

8. 2,2,6,6-Tetramethyl-4-piperidyl spiro aliphatic ethers according to claim 1 in which X is cycloalkylene.

9. A compound according to claim 1 in which X is phenylene.

10. A compound according to claim 1 in which X is polyacyl

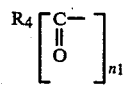

wherein $R_4$ is selected from the group consisting of alkyl having from one to about eighteen carbon atoms; cycloalkyl having from three to about eight carbon atoms; phenyl; and alkylphenyl having from seven to about eighteen carbon atoms; and $n_1$ is a number from 2 to 4.

11. A compound according to claim 1 in which X is polycarbamoyl

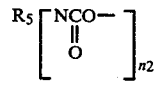

wherein $R_5$ is selected from the group consisting of alkyl having from one to about eighteen carbon atoms; cycloalkyl having from three to about eight carbon atoms; phenyl; and alkyl phenyl having from seven to about eighteen carbon atoms; and $n_2$ is a number from 2 to 4.

12. A compound according to claim 1 wherein X is

13. A compound according to claim 1 in which X is:

14. A compound according to claim 1 in which X is a di- or trivalent phosphorous acid, phosphoric acid, phosphonous acid, phosphonic acid, boric acid, and silicic acid group.

15. A compound according to claim 1 wherein $R_1$ and $R_2$ each are hydrogen.

16. A compound according to claim 1 wherein $R_1$ is

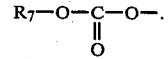

17. A compound according to claim 1 wherein $R_1$ is

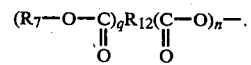

18. A compound according to claim 1 wherein $R_1$ is

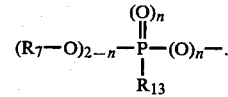

19. A compound according to claim 1 wherein $R_2$ is

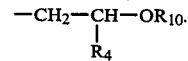

20. A compound according to claim 1 wherein $R_2$ is hydrogen.

21. A compound according to claim 1 wherein m is zero.

22. A compound according to claim 1 wherein m is 1.

23. A compound according to claim 1 wherein p is zero.

24. A compound according to claim 1 wherein p is 1.

25. A compound according to claim 23 wherein $R_3$ is —X—O—$R_1$.

26. A compound according to claim 1 having the formula:

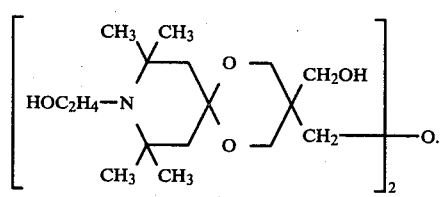

27. A compound according to claim 1 having the formula:
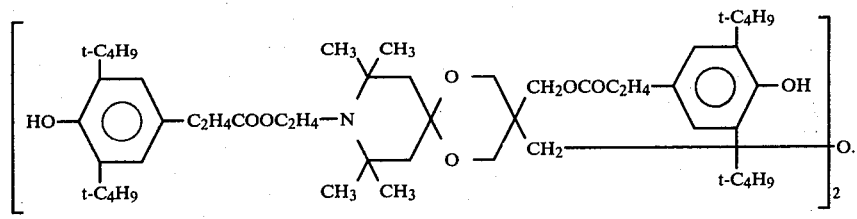
28. A compound according to claim 1 having the formula:
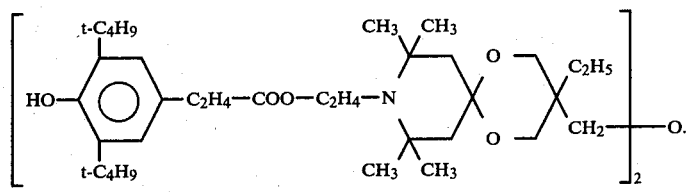
29. A compound according to claim 1 having the formula:
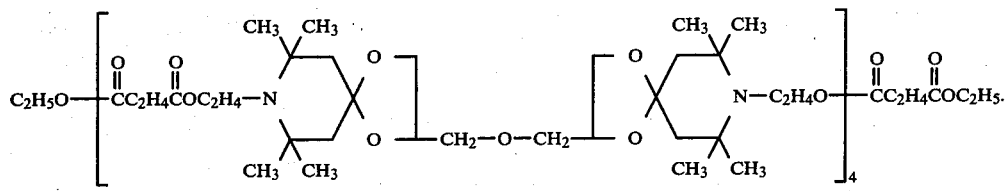
30. A compound according to claim 1 having the formula:
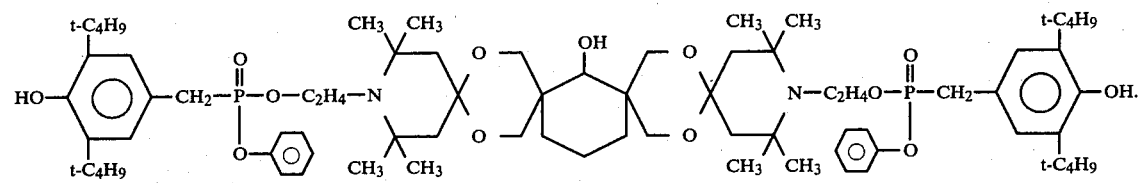
31. A compound according to claim 1 having the formula:
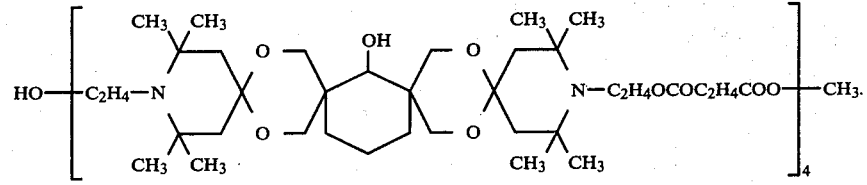
32. A compound according to claim 1 having the formula:
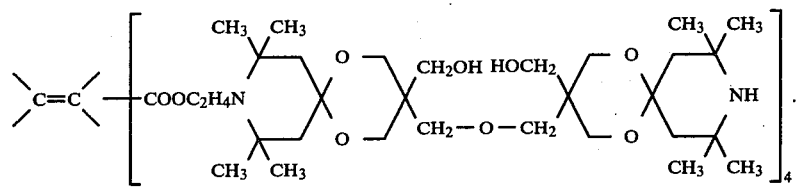
33. A compound according to claim 1 having the formula:

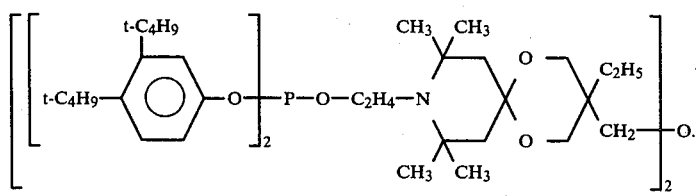

34. A compound according to claim 1 having the formula:

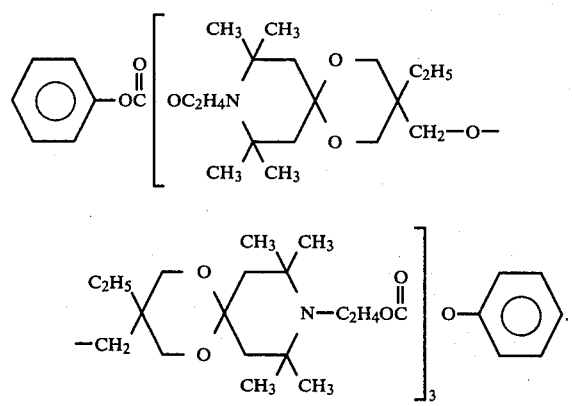

35. A polyvinyl chloride resin composition having improved resistance to deterioration when heated at 350° F., comprising a polyvinyl chloride resin formed at least in part of the recurring group:

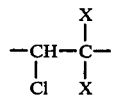

and having a chlorine content in excess of 40%, where X is either hydrogen or chlorine; and a 2,2,6,6-tetramethyl-4-piperidyl spiro aliphatic ether in accordance with claim 1.

36. A polyvinyl chloride resin composition in accordance with claim 35 in which the polyvinyl chloride resin is polyvinyl chloride homopolymer.

37. A polyvinyl chloride resin composition in accordance with claim 35 in which the polyvinyl chloride resin is a copolymer of vinyl chloride and vinyl acetate.

38. An olefin polymer composition having improved resistace to deterioration comprising an olefin polymer selected from the group consisting of polymers of alpha-olefins having from two to six carbon atoms and polystyrene, and a 2,2,6,6-tetramethyl-4-piperidyl spiro aliphatic ether in accordance with claim 1.

39. An olefin polymer composition in accordance with claim 38 wherein the polyolefin is polypropylene.

40. An olefin polymer composition in accordance with claim 38 wherein the polyolefin is polyethylene.

41. An olefin polymer composition in accordance with claim 38 wherein the polyolefin is ethylene-propylene copolymer.

42. An acrylonitrile-butadiene-styrene terpolymer having improved resistance to deterioration comprising acrylonitrile-butadiene-styrene terpolymer and a 2,2,6,6-tetramethyl-4-piperidyl spiro aliphatic ether in accordance with claim 1.

43. An ethylene-vinyl acetate copolymer composition having improved resistance to deterioration comprising ethylene-vinyl acetate copolymer and a 2,2,6,6-tetramethyl-4-piperidyl spiro aliphatic ether in accordance with claim 1.

44. A polyurethane resin composition having improved resistance to deterioration comprising a polyurethane resin and a 2,2,6,6-tetramethyl-4-piperidyl spiro aliphatic ether in accordance with claim 1.

* * * * *